(12) United States Patent
Kasda et al.

(10) Patent No.: US 12,706,191 B2
(45) Date of Patent: Aug. 11, 2026

(54) PARSING AUDIT RECORDS STORED IN A HARDWARE STORAGE DEVICE

(71) Applicant: The Johns Hopkins University, Baltimore, MD (US)

(72) Inventors: Eileen Kasda, Baltimore, MD (US); Christine Robson, Baltimore, MD (US); Sean Monaghan, Baltimore, MD (US)

(73) Assignee: The Johns Hopkins Health System Corporation, Baltimore, MD (US)

( * ) Notice: Subject to any disclaimer, the term of this patent is extended or adjusted under 35 U.S.C. 154(b) by 50 days.

(21) Appl. No.: 18/088,093

(22) Filed: Dec. 23, 2022

(65) Prior Publication Data

US 2024/0212810 A1 Jun. 27, 2024

(51) Int. Cl.
*G16H 15/00* (2018.01)
*G16H 10/60* (2018.01)

(52) U.S. Cl.
CPC ............ *G16H 15/00* (2018.01); *G16H 10/60* (2018.01)

(58) Field of Classification Search
None
See application file for complete search history.

(56) References Cited

U.S. PATENT DOCUMENTS 9,069,930 B1 6/2015 Hart
10,496,788 B2 12/2019 Amarasingham et al.
10,572,796 B2 2/2020 AlSaud et al.
10,586,437 B1 3/2020 Slavin et al.
10,621,491 B2 4/2020 Vallee
2007/0101256 A1* 5/2007 Simonyi .............. G06F 40/166 715/205
2010/0316218 A1 12/2010 Hatakeyama et al.
2014/0015855 A1 1/2014 Denney et al.
2014/0095201 A1 4/2014 Farooq et al.
2015/0120311 A1 4/2015 Mayer et al.
2017/0046651 A1 2/2017 Lin et al.
2017/0300627 A1* 10/2017 Giordano ........... G06F 21/6245

(Continued)

OTHER PUBLICATIONS

Mirshokraie, Shabnam, "Efficient JavaScript Mutation Testing," 2013 IEEE Sixth International Conference on Software Testing, Verification and Validation, pp. 74-83 (Year: 2013).*

(Continued)

*Primary Examiner* — John P Go
(74) *Attorney, Agent, or Firm* — Fish & Richardson P.C.

(57) ABSTRACT

A computer-implemented method includes: receiving a request to perform an audit on data describing a medical safety event; obtaining an initial audit record based on the request; parsing the initial audit record to identify a structure of the initial audit record; identifying, from the structure, one or more fields that describe one or more properties of the medical safety event; identifying a mutation object based on the one or more fields, with the mutation object describing an initial content of the data; determining a first change of the data from the initial content to a first updated content; updating the mutation object to describe the first updated content; obtaining a first updated audit record based on the first updated content of the data; storing the mutation object describing the first updated content; and storing the initial audit record and the first updated audit record.

19 Claims, 10 Drawing Sheets

(56) References Cited

U.S. PATENT DOCUMENTS

| | | | | |
|---|---|---|---|---|
| 2018/0025116 | A1 | 1/2018 | Carrington et al. | |
| 2018/0032917 | A1 | 2/2018 | Hagen et al. | |
| 2018/0253464 | A1 | 9/2018 | Kohli et al. | |
| 2019/0122144 | A1 | 4/2019 | Kabeya et al. | |
| 2019/0272392 | A1* | 9/2019 | Falah | G06F 21/645 |
| 2019/0280855 | A1* | 9/2019 | Tong | H04L 9/0637 |
| 2019/0340369 | A1* | 11/2019 | Hadi | G06V 40/33 |
| 2019/0349321 | A1 | 11/2019 | Cai et al. | |
| 2020/0112427 | A1* | 4/2020 | Nakamura | H04L 9/0637 |
| 2020/0176093 | A1 | 6/2020 | Kuchibotla et al. | |
| 2020/0226321 | A1 | 7/2020 | Burns et al. | |
| 2020/0265273 | A1 | 8/2020 | Wei et al. | |
| 2021/0042678 | A1 | 2/2021 | Geppert et al. | |
| 2021/0263900 | A1 | 8/2021 | Joyce et al. | |
| 2021/0304860 | A1 | 9/2021 | Hart et al. | |
| 2021/0319895 | A1* | 10/2021 | Joao | G06F 16/182 |
| 2022/0005568 | A1 | 1/2022 | Aldairy et al. | |
| 2022/0156249 | A1* | 5/2022 | Luedtke | G06F 16/2379 |
| 2024/0079102 | A1 | 3/2024 | Goravar et al. | |
| 2024/0211800 | A1 | 6/2024 | Kasda et al. | |

OTHER PUBLICATIONS

International Search Report and Written Opinion in International Appln. No. PCT/US2023/084831, mailed on Apr. 12, 2024, 13 pages.

International Search Report and Written Opinion in International Appln. No. PCT/US2023/084817, mailed on Apr. 1, 2024, 8 pages.

Fong et al., "Making Sense of Patient Safety Event Data: Leveraging the Power of Visualization," Proceedings of the Human Factors and Ergonomics Society Annual Meeting, Oct. 17, 2014, 58(1):723-727.

Hansen et al., "Near-Real Time Monitoring of Reports regarding Patient Safety Incidents in Hospitals using a Web-based Interface," Presented at Proceedings of the 13th Scandanavian Conference on Health Informatics, Tromsø, Norway, Jun. 15-17, 2015; Linköping Electronic Conference Proceedings, Jun. 26, 2015, 115:6-11.

SciKit-Learn.org [online], "sklearn.metrics.fbeta_score," available on or before Oct. 29, 2021 via Internet Archive: Wayback Machine URL<https://web.archive.org/web/20211029053620/https://scikit-learn.org/stable/modules/generated/sklearn.metrics.fbeta_score.html>, retrieved on Oct. 9, 2023, retrieved from URL<https://scikit-learn.org/stable/modules/generated/sklearn.metrics.fbeta_score.html>, 2 pages.

* cited by examiner

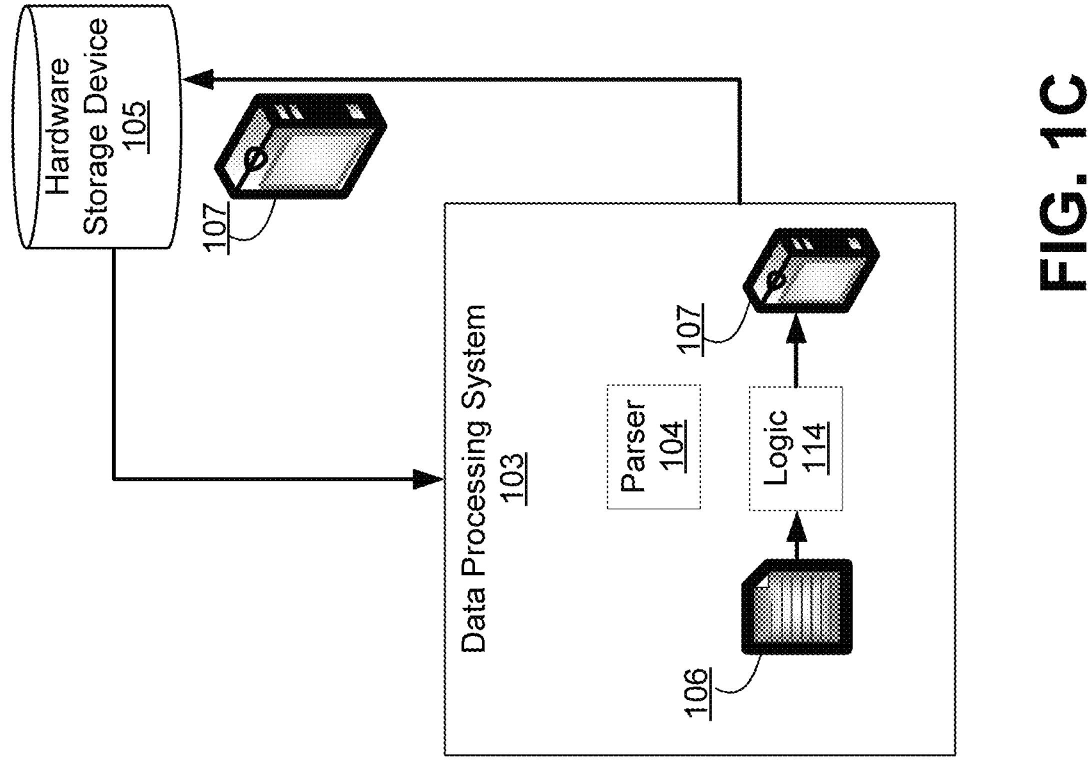
FIG. 1C
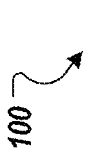

PARSING AUDIT RECORDS STORED IN A HARDWARE STORAGE DEVICE

BACKGROUND

Event reporting plays an important role in daily operations of many institutions. For example, in the healthcare industry, a healthcare institution may receive numerous reports from staff about medical safety events occurring on patients or facilities every day. To ensure quality of healthcare service and comply with regulations, healthcare institutions often need to perform audits on the medical safety event reports and keep track the changes of each logged report.

SUMMARY

In accordance with one aspect of the present disclosure, a computer-implemented method includes receiving a request to perform an audit on data describing a medical safety event. The method includes obtaining an initial audit record based on the request. The method includes parsing the initial audit record to identify a structure of the initial audit record. The method includes identifying, from the structure, one or more fields that describe one or more properties of the medical safety event. The method includes identifying a mutation object based on the one or more fields of the initial audit record, with the mutation object describing an initial content of the data. The method includes determining a first change of the data from the initial content to a first updated content. The method includes updating the mutation object to describe the first updated content. The method includes obtaining a first updated audit record based on the first updated content of the data. The method includes storing, in a hardware storage device, the mutation object describing the first updated content. The method includes storing, in the hardware storage device, the initial audit record and the first updated audit record.

In some implementations, the one or more properties include an action of the audit.

In some implementations, the one or more properties include one or more references to the medical safety event.

In some implementations, the mutation object includes an event description, a mutation status indicator, and a mutation action indicator.

In some implementations, updating the mutation object to describe the first updated content includes: setting the event description to include the first updated content of the data and the first change; setting the mutation status indicator to indicate a combination of the first updated content and the first change; and setting the mutation action indicator to indicate a first update of the mutation object.

In some implementations, the method further includes determining a second change of the data from the first updated content to a second updated content; and updating the mutation object to describe the second updated content.

In some implementations, updating the mutation object to describe the second updated content includes: setting the event description to include the second updated content of the data, the first change, and the second change; setting the event description to remove the first updated content of the data; setting the mutation status indicator to indicate a combination of the second updated content and the second change, and to indicate a difference corresponding to the first change; and setting the mutation action indicator to indicate the first update of the mutation object and a second update of the mutation object.

In some implementations, the initial audit record and the first updated audit record are stored in a format of an expression language.

In some implementations, the method further includes obtaining a second updated audit record based on the second updated content of the data; and storing, in the hardware storage device, the second updated audit record.

In some implementations, the mutation object describes the initial content of the data by: setting the event description to include the initial content; setting the mutation status indicator to indicate a full description of the initial content; and setting the mutation action indicator to indicate a creation of the mutation object.

In one aspect, a non-transitory computer-readable medium stores program instructions that cause a data processing system to perform operations. In some implementations, these operations are similar to one or more of those of the computer-implemented method described above.

BRIEF DESCRIPTION OF THE DRAWINGS

FIGS. 1B-1E illustrate example data flows for managing audit records, according to some implementations.

Figures are not drawn to scale. Like reference numbers refer to like components.

DETAILED DESCRIPTION

A healthcare institution may record hundreds of medical safety events every day. Some of these records are newly-created while some are updates on existing records. For example, when a patient is admitted to a hospital, a receptionist may create a report that describes the admission of the patient, while a nurse may later update the report with a follow-up note about the patient's condition after performing initial screening. To keep track of the creation and changes of the records, the healthcare institution typically develops and maintains an electronic data processing system to store data describing the events.

The data in the electronic data processing system may be subject to audits from time to time. In an audit, a reviewer may want to access not only the latest content of the record of an event, but the historic evolution of records of the same event. For example, the reviewer may want to see not only the latest condition of the patient but all steps the hospital has taken since the patient's admission. Accordingly, there is a need for the electronic data processing system to be able to store a large amount of event data and quickly present the historic changes of data of a given event.

This disclosure is made in light of the above needs. As described in detail below, implementations of this disclosure use a mutation object to track event data changes and facilitate maintenance of audit records. Thanks to one or more features of this disclosure, users and administrators of the electronic data processing system can quickly identify the nature of event data changes and estimate the amount of event data changes over a period of time using a relatively small amount of data storage resources. As such, implementations of this disclosure can advantageously improve the efficiency of medical safety event auditing.

Figure 1A:
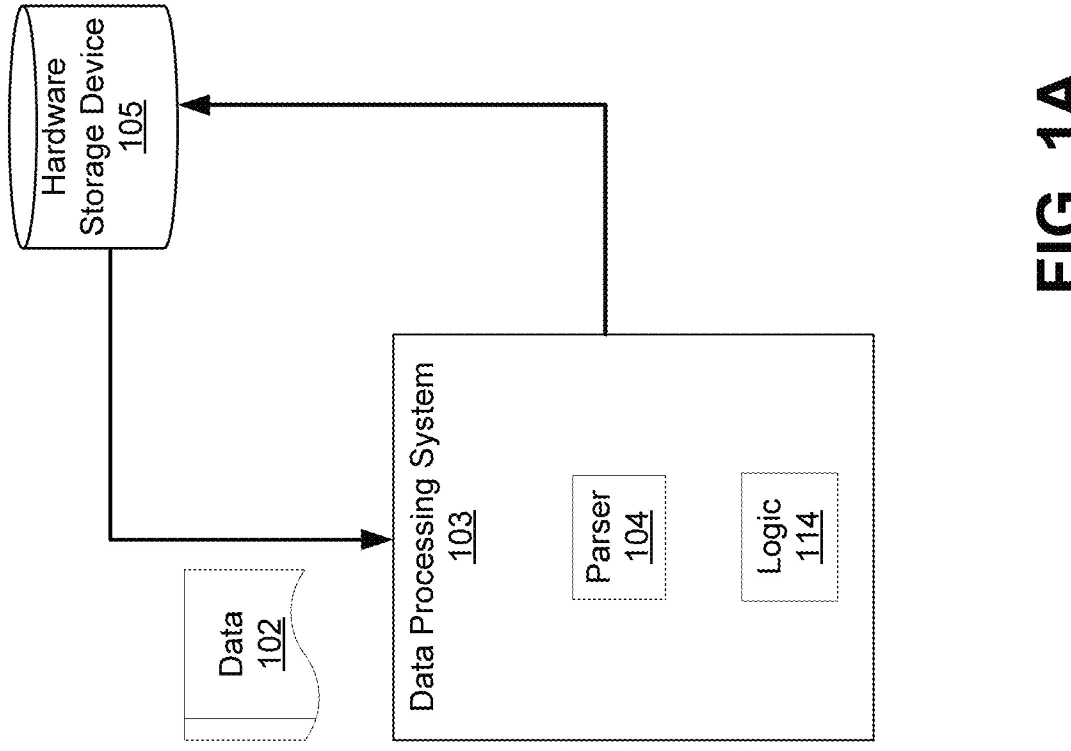
FIG. 1A illustrates a diagram of an example system for managing audit records, according to some implementations.
Figure 1A:

FIG. 1A illustrates a diagram of an example system 100 for managing audit records, according to some implementations. System 100 can be implemented on one or more computers, mobile devices, or network devices. System 100 primarily includes 2 components: data processing system 103 and hardware storage device 105.

In some implementations, data processing system 103 includes computer hardware and software for accessing and processing event data, such as data 102, stored in hardware storage device 105. Data 102 describe one or more events, such as safety-related events happening on a healthcare facility. Each entry of data 102 can be structured to have one or more fields that describe an event from various aspects. For example, the fields can include Event ID, Date, Time, Reporter ID, Description, and Note. In particular, the Description of an event can be narrative free text, with which a reporter uses narrative language to describe that which happened at the event. Values of some fields can be modified to reflect, e.g., updates of the described event. For example, after a newly-admitted patient receives initial screening, a nurse may add to the "Note" field of a corresponding data entry a description of the initial screening results, while modifying the Date, Time, and Reporter ID fields of the data entry.

In some implementations, data processing system 103 includes parser 104 to extract contents of one or more fields of data 102 and compare the contents with those previously stored in hardware storage device 105 to identify a change. Data processing system 103 also includes logic 114, formed by software code and/or hardware circuitry, to execute one or more algorithms for tracking the recording the identified change. Example operations involving parser and logic 114 are described below with reference to FIGS. 1B-1E.

FIGS. 1B-1E illustrate example data flows for managing audit records, according to some implementations. FIGS. 1B-1E assume that the data flows illustrated occur in system 100.

Figure 1B:
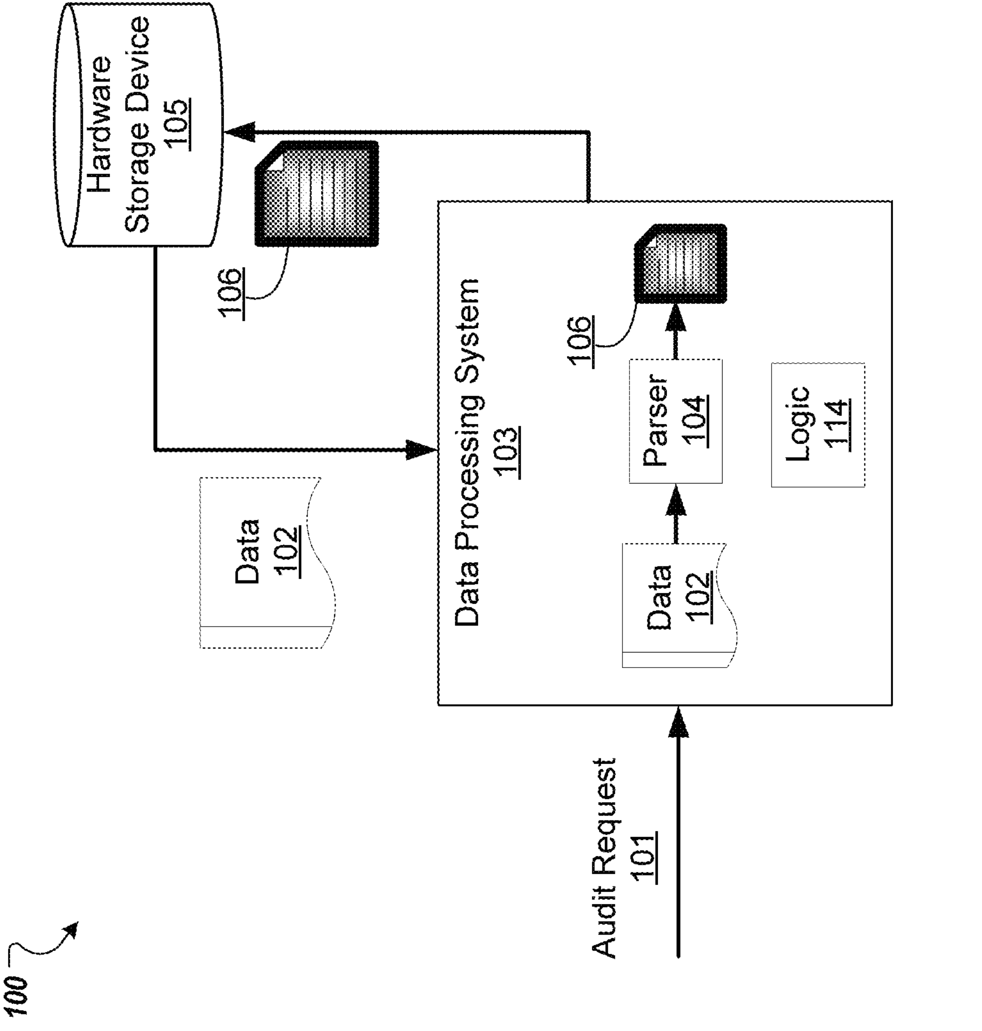

As shown in FIG. 1B, in some implementations, data processing system 103 receives a request, such as audit request 101, to audit data 102. Audit request 101 can be received from, e.g., a user interface that connects data processing system 103 to an external device or network. In some implementations, audit request 101 specifies values or a range of values of one or more fields of data 102. For example, audit request 101 can specify that the audit is to be conducted on event data with a Date between Jan. 1, 2020 and Dec. 31, 2020. In some alternative implementations, audit request 101 does not specify the values of any fields, and the audit may be conducted on some or all of event data according to the settings of data processing system 103.

Upon receipt of audit request 101, data processing system 103 can conduct an audit on data 102 accordingly and obtain one or more audit records, such as audit record 106. Audit record 106 can be structured with one or more fields that describe one or more properties of the audit. Example properties include identifier (ID) of the audit, time of creation of the audit record, content of the audited event data, and one or more references to the audited event data. In some implementations, entries of audit record 106 are compiled chronologically in a log file, which may be a human-readable text file or a computer-readable binary file. In some implementations, audit record 106 is formatted and stored according to an expression language, such as Spring Expression Language. The expression language can allow a user to conveniently access the log file to classify and analyze the entries of audit record 106. Audit record 106 can be stored in hardware storage device 105.

In some implementations, data processing system 103 retrieves (and/or read) from volatile memory and/or non-volatile memory audit record 106 and parses audit record 106 to identify the fields and the associated values based on the structure of audit record 106. For example, parser 104 detects the following data structure: ID (0012); Created (06:00, Jan. 1, 2020) from data 102. In this example structure, "ID" and "Created" each denote a field, while "0012" and "06:00, Jan. 1, 2020" are values corresponding to the fields. The symbols "( )" and ";" delineate the two fields of the structure.

Moving to FIG. 1C, data processing system 103 can, based on the identified fields of audit record 106, use logic 114 to identify a mutation object, such as mutation object 107. Mutation object 107 can be included as part of audit record 106 or can be separately generated by data processing system 103 based on audit record 106. Mutation object 107 can describe a content of audited data 102 and can be structured to track the changes of the content of data 102. Once identified, mutation object 107 can be stored in hardware storage device 105.

Figure 1D:
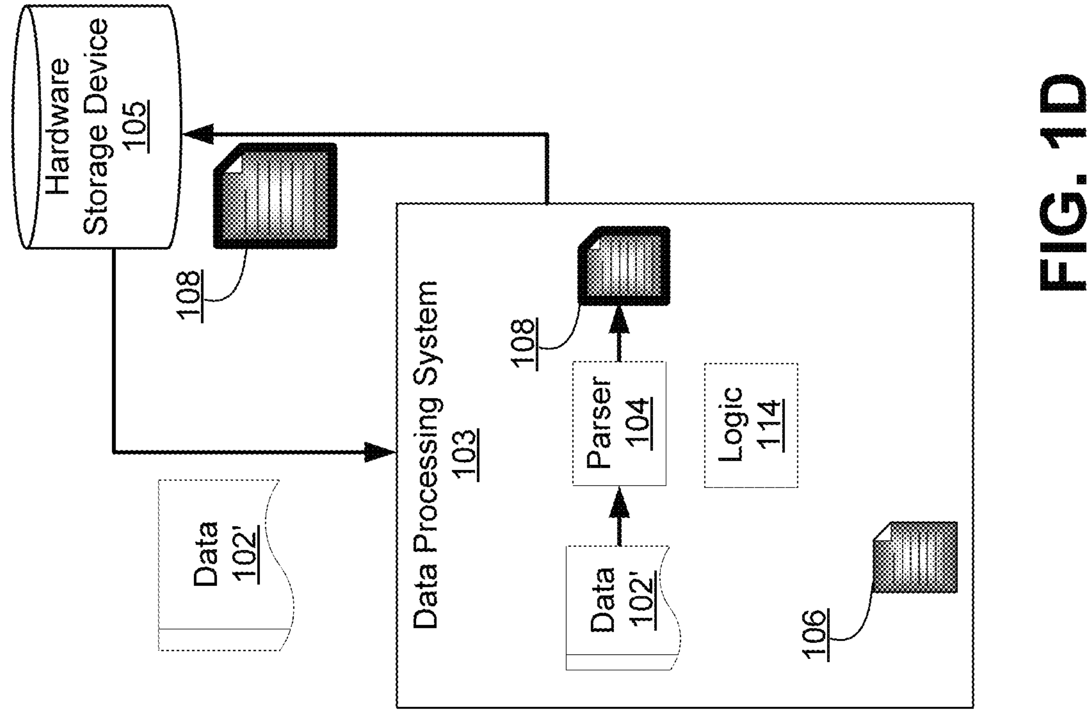
Figure 1D:
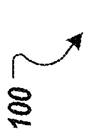

Moving to FIG. 1D, data processing system 103 can detect a change of the content of data 102, now denoted as 102'. For example, data processing system 103 can periodically access hardware storage device 105, compare the latest content of data 102 with a previous version, and detect that one or more fields of data 102 have been updated. Upon detection of data 102' resulting from the change, parser 104 parses data 102' and obtains one or more audit records, such as audit record 108, to describe the change. In some implementations, entries of audit record 108 are compiled chronologically in a log file, which may be the same log file where entries of audit record 106 are compiled. Similar to audit record 106, audit record 108 can be stored in hardware storage device 105.

Figure 1E:
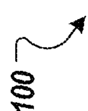
Figure 1E:
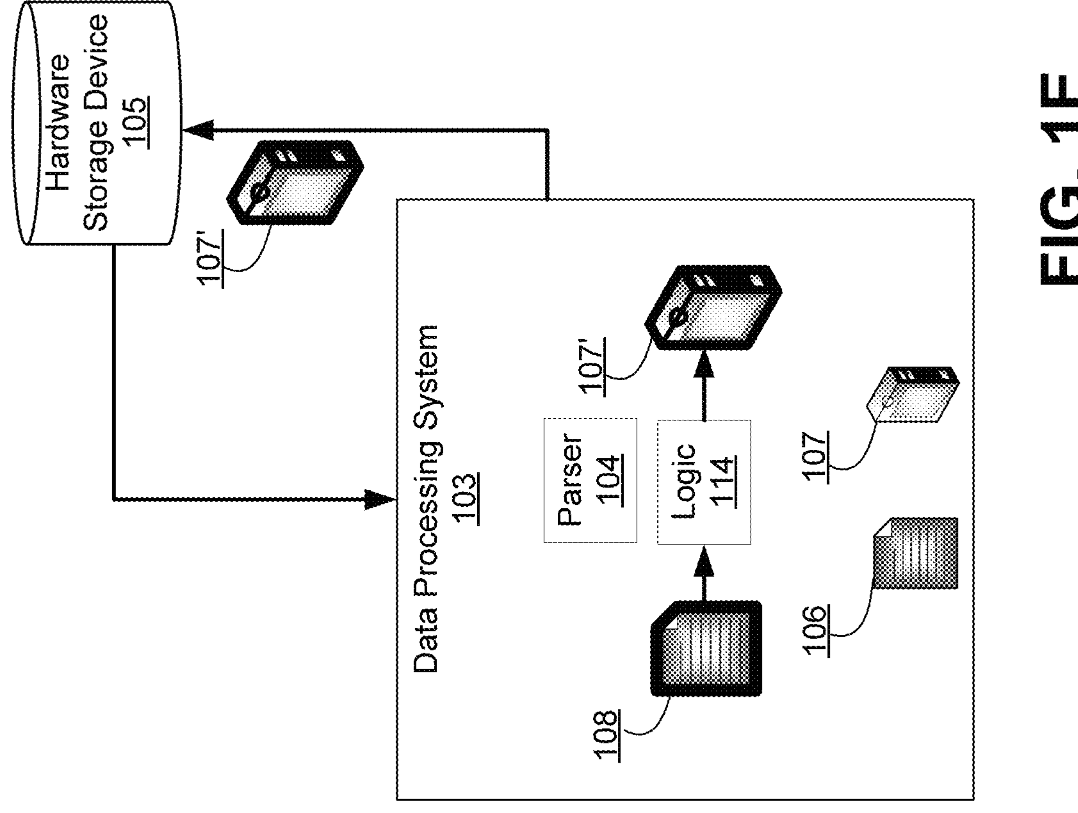
Figure 1E:

Moving to FIG. 1E, logic 114 can update mutation object 107, denoted as mutation object 107', to describe the content of data 102' after the change. For example, mutation object 107' can include the full content of data 102' after the change, or can include only the difference of the content resulting from the change. Mutation object 107' can be stored in hardware storage device 105. In some implementations, mutation object 107' overwrites the storage space for mutation object 107. As such, less storage is needed for tracking the data change using a mutation object.

Figure 2:
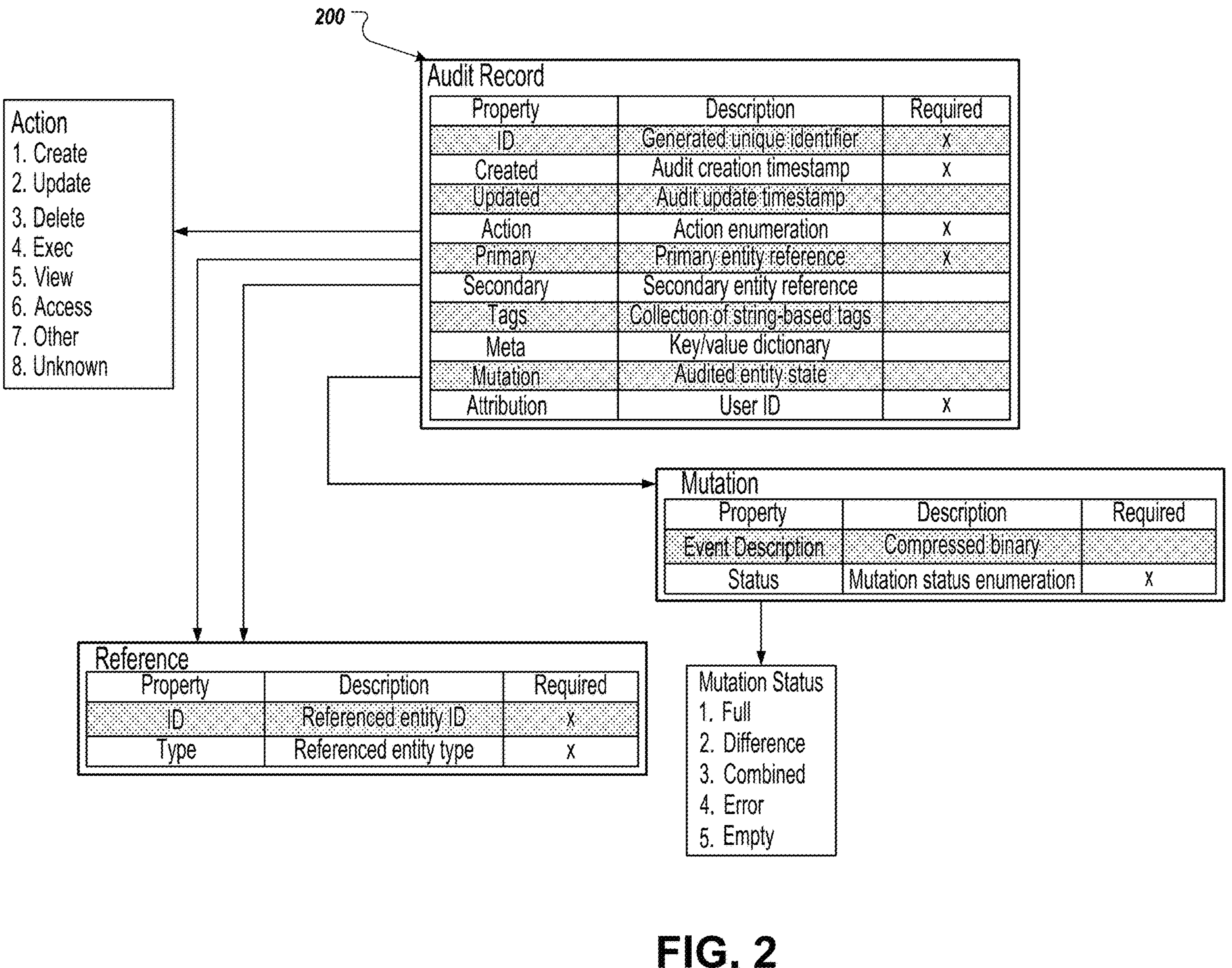
FIG. 2 illustrates an example structure of audit records, according to some implementations.

FIG. 2 illustrates an example structure 200 of audit record according to some implementations. Structure 200 can be applicable to audit records 106 and 108 described with reference to FIG. 1A.

As shown in FIG. 2, structure 200 has fields describing the properties (the "Property" column) of an audit. These fields can include one or more of: ID, Created, Updated, Action, Primary, Secondary, Tags, Meta, Mutation, and Attribution. Some of these fields are required to have a value while some are not, as indicated by the "Required" column. Description of these fields are under the "Description" column. It is noted that the fields of structure 200 are only examples and may or may not be present in other implementations.

In some implementations, structure 200 has a field Action to describe the latest action on the audit record. The value of Action can be one of: Create, Update, Delete, Exec, View, Access, Other, Unknown. For example, when a user sends an audit request to perform a new audit, the value of Action can be Create to indicate the creation of a new audit record; when a user modifies the audit request to conduct an updated audit, the value of Action can be Update to indicate the update of an existing audit record.

In some implementations, structure 200 has a field Primary to describe a primary reference to an audited entity (e.g., event data entry) and a field Secondary to describe a secondary reference to the audited entity. Each of fields Primary and Secondary can have an ID field to identify the entity and a Type field to indicate the type of the entity. For example, when a user performs an audit on an event and creates a comment for the event, the field Primary can indicate the audited event data entry itself while the field Secondary can indicate the created comment. To do so, the ID field of Primary can equal the value of Event ID of the event data entry and the Type field of Primary can be "Event." Correspondingly, the ID field of Secondary can equal an ID assigned to the created comment and the Type field of Secondary can be "Comment."

In some implementations, structure 200 has a field Mutation to describe the changes of the audited event data. The field Mutation can be instantiated as a mutation object that includes an Event Description and a Status indicator. The Status indicator can have a value of one of: Full, Difference, Combined, Error, and Empty. Each of these statuses can correspond to a nature of the value of Event Description. For example, when Event Description provides a full description of an audited event data entry, then the Status indicator can be Full; when Event Description provides only the difference of the description between the time of audit and an earlier time, then the Status indicator can be Difference; when Event Description provides both the full description and the difference between the time of audit and an earlier time, then the Status indicator can be Combined.

In addition to Event Description and the Status indicator, a mutation object can have other fields or properties. In some implementations, a mutation object has an Action indicator that describes an action taken on the mutation object. The value of the Action indicator can be Create to indicate the creation of the mutation object, or Update to indicate a change made to the mutation object. More details of the roles of Event Description, the Status indicator, and the Action indicator of a mutation object are described with reference to FIGS. 3A and 3B.

Figure 3A:
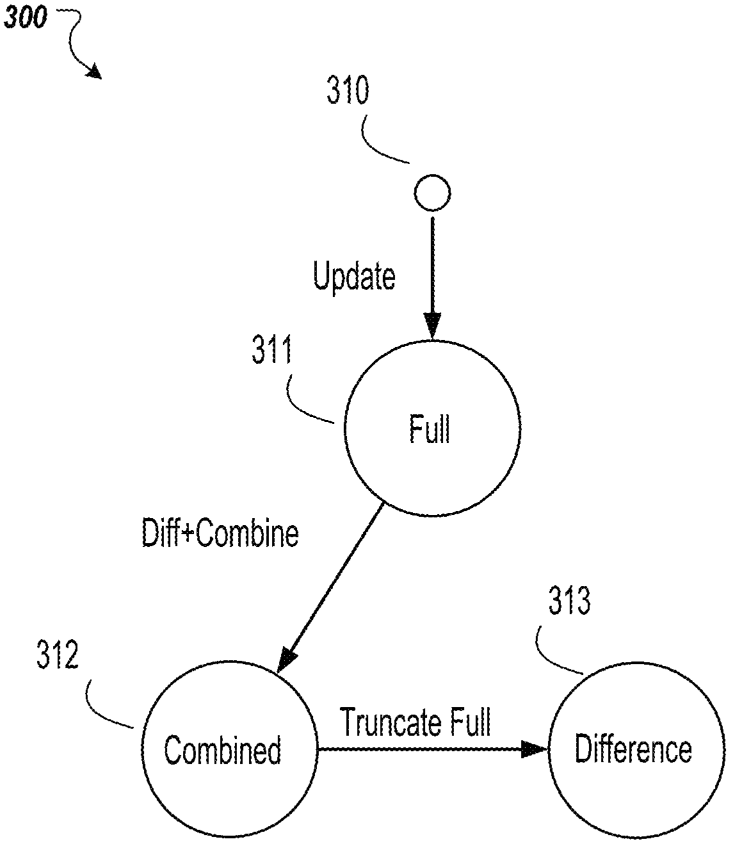
FIG. 3A illustrates an example transition diagram of mutation statuses and mutation actions, according to some implementations.

FIG. 3A illustrates an example transition diagram 300 of mutation statuses and mutation actions, according to some implementations. Transition diagram 300 can be implemented as a computer program executable by, e.g., data processing system 103 of FIG. 1A. The mutation statuses and mutation actions can correspond to one or more values of the Status indicator and the Action indicator described with reference to FIG. 2.

At 310, an audit record is obtained to describe an audit performed on an event data entry. Correspondingly, a mutation object is instantiated, with the Event Description field storing the full content of a description of the audited event. The mutation object can be considered as an initial instance in the transition.

At 311, the event data entry is updated with a change of content. Corresponding to the change of the event data entry, the audit record is updated and becomes an updated audit record. Upon detecting the change, the mutation object is updated to additionally include a second instance reflecting the change. The second instance has its Event Description field storing the full content of the description of the event after the change. In the meantime, the mutation object updates the Action indicator of the second instance to Update and updates the Status indicator of the second instance to Full.

At 312, the mutation object compares the description of the event before and after the change and obtains a difference. The mutation object then updates the Event Description field of the second instance to include both: the full content of the description of the event after the change, and the difference. In the meantime, the mutation object updates the Status indicator of the second instance to Combined.

At 313, the event data entry is updated with another change of content. Corresponding to the second change, the audit record is again updated. Upon detecting the second change, the mutation object is updated to additionally include a third instance reflecting the second change. The third instance has its Event Description field storing the full content of the description of the event after the second change. Also, the mutation object compares the description of the event before and after the second change and obtains a difference between the two. This difference is also stored in the Event Description field of the third instance. As such, the mutation object updates the Action indicator of the third instance to Update and updates the Status indicator of the second instance to Combined.

Also in 313, because of the Combined status of the third instance, it is no longer needed to store the full description of the event after the first change but before the second change. Therefore, the mutation object truncates, from the Combined event description in the second instance, the full content of the event description after the first change but before the second change. As a result of the truncation, only the difference of description caused by the first change is remaining in the Event Description field of the second instance. Correspondingly, the mutation object updates the Status indicator of the second instance from Combined to Difference ("Diff").

Figure 3B:
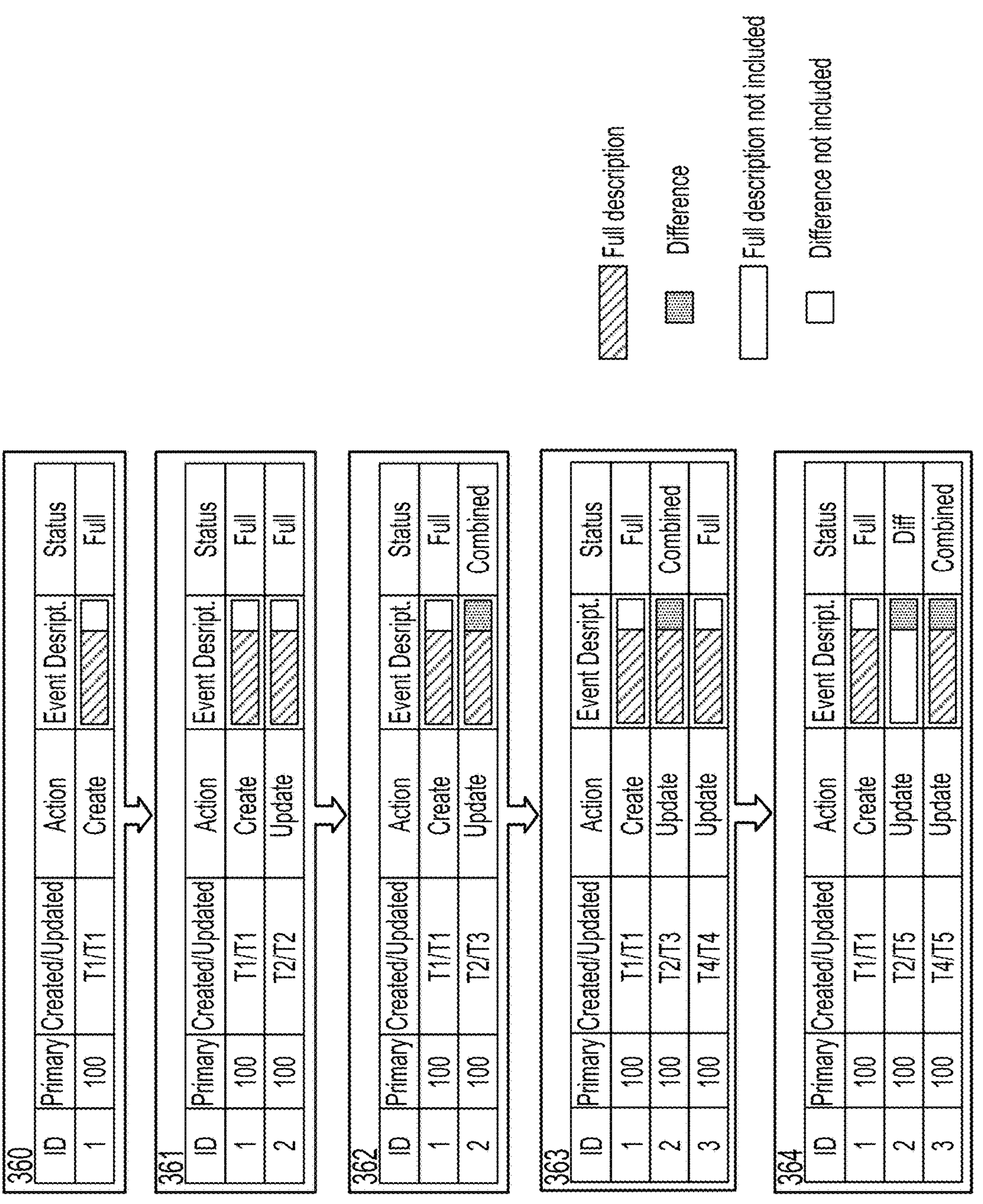
FIG. 3B illustrates an example flow of updating a mutation object based on changes of event data, according to some implementations.

FIG. 3B illustrates an example flow 350 of updating a mutation object based on changes of event data, according to some implementations. Flow 350 can be similar to transition diagram 300 of FIG. 3A, and can be implemented as a computer program executable by, e.g., data processing system 103 of FIG. 1A.

As shown in table 360, at time T1, an audit record with a primary reference of 100 is obtained to describe an audit performed on an event data entry. Correspondingly, a mutation object is created at T1 to include an initial instance (ID=1). The "Action" column is marked with "Create" to indicate that the action at T1 is the creation of the mutation object. Because no further updates have been performed on the initial instance, the "Created/Updated" column is marked with "T1/T1." The initial instance has its Event Description field storing the full description of the audited event data entry. Accordingly, the Status indicator of the initial instance is Full. The state of the mutation object illustrated in table 360 can be similar to state 310 of FIG. 3A.

As shown in table 361, at time T2, the event data entry is updated with a first change of content. Upon detecting the first change, the mutation object is updated to additionally include a second instance (ID=2) reflecting the first change, as shown in the second row of table 361. The "Action" column of the second row is marked with "Update" to indicate that the action at T2 is an update of the mutation object. Because no further updates have been performed on the second instance, the "Created/Updated" column at the second row is marked with "T2/T2." The second instance has its Event Description field storing the full content of the description of the event after the first change. Accordingly, the Status indicator of the second instance is Full. The state of the mutation object illustrated in table 361 can be similar to state 311 of FIG. 3A.

As shown in table 362, at time T3, the mutation object compares the description of the event before and after the first change and obtains a difference. The mutation object then updates the Event Description field of the second instance to include both: the full content of the description of the event after the change, and the difference. In the meantime, the mutation object updates the Status indicator of the second instance to Combined. Because the second instance is created at T2 and updated at T3, the "Created/Updated" column of the second row is marked with "T2/T3." The state of the mutation object illustrated in table 362 can be similar to state 312 of FIG. 3A.

As shown in table 363, at time T4, the event data entry is updated with another change of content. Upon detecting the second change, the mutation object is updated to additionally include a third instance (ID=3) reflecting the second change. Because no further updates have been performed on the third instance, the "Created/Updated" column at the second row is marked with "T4/T4." The third instance has its Event Description field storing the full content of the description of the event after the second change. Accordingly, the Status indicator of the third instance is Full. The state of the mutation object illustrated in table 363 can be similar to an intermediate state during the transition from 312 to 313 in FIG. 3A.

As shown in table 364, at time T5, the mutation object truncates, from the Combined event description in the second instance, the full content of the event description after the first change but before the second change. As a result of the truncation, only the difference of description caused by the first change is remaining in the Event Description field of the second instance. Correspondingly, the mutation object updates the Status indicator of the second instance from Combined to Diff and records the time of the update by changing the Created/Updated" column at the second row to "T2/T5."

Keeping with table 364, in the meantime of updating the second instance, the mutation object compares the event description before and after the second change and obtains a difference between the two. The mutation object then updates the Event Description field of the third instance to also store this difference. As such, the mutation object updates the Status indicator of the third instance to Combined and records the time of update by changing the Created/Updated" column at the third row to "T4/T5." The state of the mutation object illustrated in table 364 can be similar to state 313 in FIG. 3A.

The transitions of statuses and the corresponding actions described with reference to FIGS. 3A and 3B can continue as more changes are detected on the event data entry. In general, the mutation object can have (i) an initial instance having a status Full and storing the full content of the initial event description at the time of the audit, (ii) one or more intermediate instances (the second instance in the examples of FIGS. 3A and 3B) each having a status Diff and storing only the difference of the description before and after a corresponding change, and (iii) a latest instance (the third instance in the examples of FIGS. 3A and 3B) having a status Combined and storing a combination of the full content of the description after a latest change and a difference caused by the latest change. This algorithm can save computing and storage resources because only the differences, not the full event descriptions, are stored by the mutation object for the changes tracked by the intermediate changes.

Figure 4:
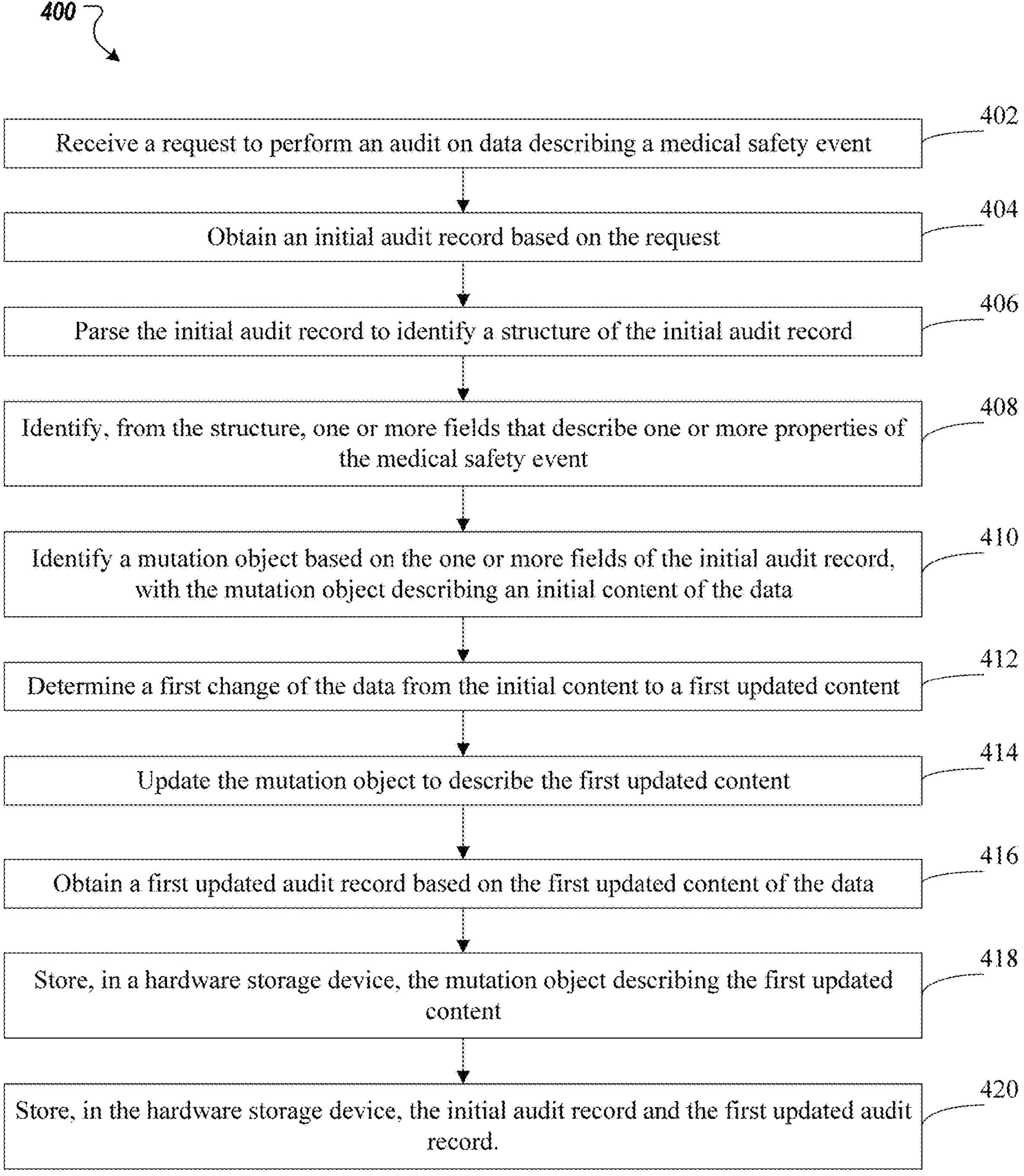
FIG. 4 illustrates a flowchart of an example method, according to some implementations.

FIG. 4 illustrates a flowchart of an example method 400, according to some implementations. Method 400 can be performed, for example, by data processing system 103 or any suitable system, environment, software, hardware, or a combination of systems, environments, software, and hardware, as appropriate. In some implementations, various steps of method 400 can be run in parallel, in combination, in loops, or in any order.

At 402, method 400 involves receiving a request to perform an audit on data describing a medical safety event. The request can be similar to audit request 101 and the data can be similar to data 102.

At 404, method 400 involves obtaining an initial audit record based on the request. The initial audit record can be similar to audit record 106.

At 406, method 400 involves parsing the initial audit record to identify a structure of the initial audit record. The structure can be similar to structure 200 of FIG. 2.

At 408, method 400 involves identifying, from the structure, one or more fields that describe one or more properties of the medical safety event. The one or more fields can include one or more of those described with reference to FIG. 2.

At 410, method 400 involves identifying a mutation object based on the one or more fields of the initial audit record, with the mutation object describing an initial content of the data. The mutation object can be similar to mutation object 107 of FIG. 1A, or can be similar to those described with reference to FIGS. 3A and 3B. The initial content can be similar to that described in the Event Description field of the mutation object.

At 412, method 400 involves determining a first change of the data from the initial content to a first updated content.

At 414, method 400 involves updating the mutation object to describe the first updated content. The mutation object after the update can be similar to mutation object 107'.

At 416, method 400 involves obtaining a first updated audit record based on the first updated content of the data. The first updated audit record can be similar to audit record 108.

At 418, method 400 involves storing, in a hardware storage device, the mutation object describing the first updated content. The hardware storage device can be similar to hardware storage device 105.

At 420, method 400 involves storing, in the hardware storage device, the initial audit record and the first updated audit record. The storing can involve compiling the initial audit record and the first updated audit record chronologically in a log file.

In addition to the operations involved in method 400, various operations can be performed as more event data entries are audited and more changes of event data are detected. The performance of these operations can be consistent with the state transitions described with reference to FIGS. 3A and 3B.

Figure 5:
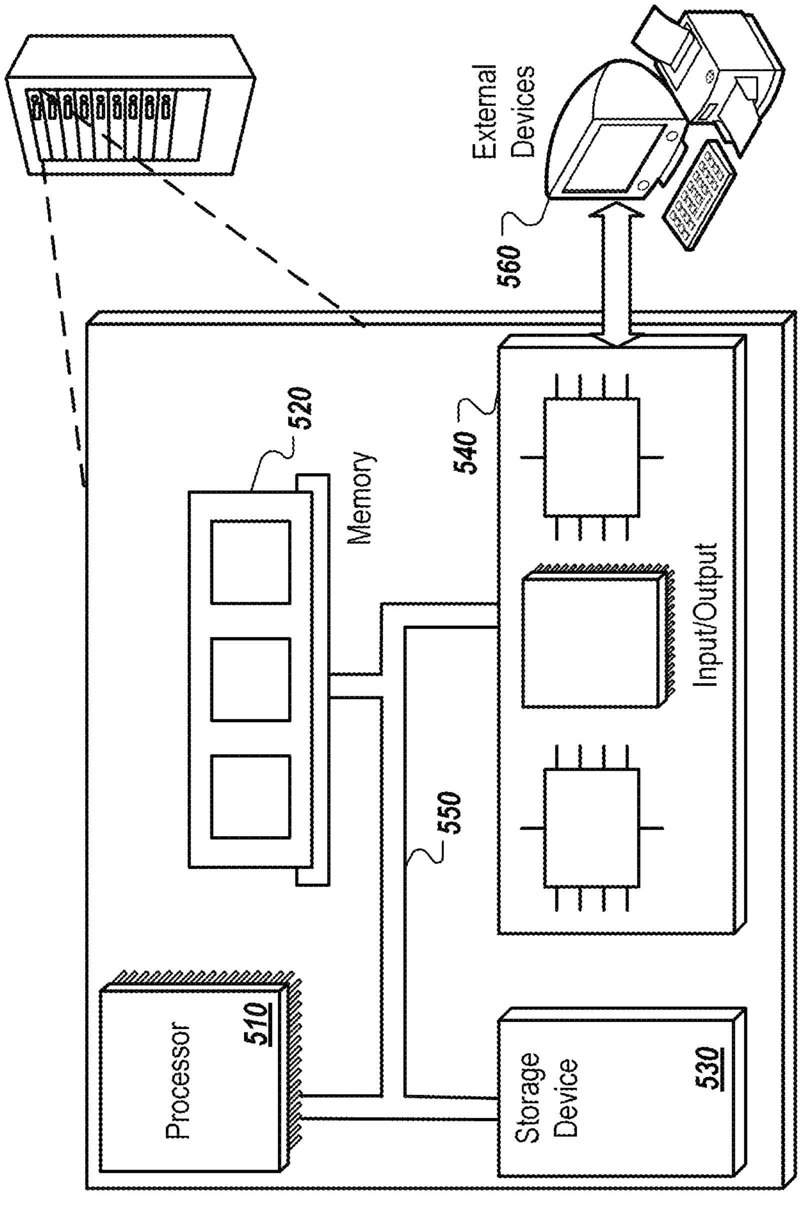
FIG. 5 illustrates a block diagram of an example computer system, according to some implementations.
Figure 5:
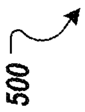

FIG. 5 is a block diagram of an example computer system 500 in accordance with embodiments of the present disclosure. The system 500 can be configured to implement data processing system 103 and/or hardware storage device 105. The system 500 includes a processor 510, a memory 520, a storage device 530, and one or more input/output interface devices 540. Each of the components 510, 520, 530, and 540 can be interconnected, for example, using a system bus 550.

The processor 510 is capable of processing instructions for execution within the system 500. The term "execution" as used here refers to a technique in which program code causes a processor to carry out one or more processor instructions. In some implementations, the processor 510 is a single-threaded processor. In some implementations, the processor 510 is a multi-threaded processor. The processor 510 is capable of processing instructions stored in the memory 520 or on the storage device 530. The processor 510 may execute operations such as those described with reference to other figures described herein.

The memory 520 stores information within the system 500. In some implementations, the memory 520 is a computer-readable medium. In some implementations, the memory 520 is a volatile memory unit. In some implementations, the memory 520 is a non-volatile memory unit.

The storage device 530 is capable of providing mass storage for the system 500. In some implementations, the storage device 530 is a non-transitory computer-readable medium. In various different implementations, the storage device 530 can include, for example, a hard disk device, an optical disk device, a solid-state drive, a flash drive, magnetic tape, or some other large capacity storage device. In some implementations, the storage device 530 may be a cloud storage device, e.g., a logical storage device including one or more physical storage devices distributed on a network and accessed using a network. In some examples, the storage device may store long-term data. The input/output interface devices 540 provide input/output operations for the system 500. In some implementations, the input/output interface devices 540 can include one or more of a network interface devices, e.g., an Ethernet interface, a serial communication device, e.g., an RS-232 interface, and/or a wireless interface device, e.g., an 802.11 interface, a 3G wireless modem, a 4G wireless modem, a 5G wireless modem, etc. A network interface device allows the system 500 to communicate, for example, transmit and receive data. In some implementations, the input/output device can include driver devices configured to receive input data and send output data to other input/output devices, e.g., keyboard, printer and display devices 560. In some implementations, mobile computing devices, mobile communication devices, and other devices can be used.

A server can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

In some examples, the system 500 is contained within a single integrated circuit package. A system 500 of this kind, in which both a processor 510 and one or more other components are contained within a single integrated circuit package and/or fabricated as a single integrated circuit, is sometimes called a microcontroller. In some implementations, the integrated circuit package includes pins that correspond to input/output ports, e.g., that can be used to communicate signals to and from one or more of the input/output interface devices 540.

Although an example processing system has been described in FIG. 5, implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. In an example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "computing device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as standalone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a GNSS sensor or receiver, or a portable storage device such as a universal serial bus (USB) flash drive.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

While this specification includes many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

What is claimed is:

1. A computer-implemented method, comprising:

receiving a request to perform an audit on data describing a medical safety event of a plurality of medical safety events within a healthcare institution;

obtaining, from a hardware storage device storing a plurality of audit records based on the request, an initial audit record corresponding to the medical safety event of the plurality of medical safety events;

parsing, by a parser, fields of the initial audit record to identify a structure of the initial audit record;

accessing, from a database from the structure of the parsed fields, one or more fields that describe one or more properties of the medical safety event;

instantiating a mutation object based on the one or more accessed fields of the initial audit record, with the mutation object describing an initial content of the data;

accessing, from a database by the mutation object according to executable logic for identifying differences between data files, a first change of the data from the initial content to a first updated content, wherein the first change of the data represents each point of difference between the initial content and the first updated content;

overwriting, in memory, storage space for the mutation object with an updated mutation object that describes the first updated content, the initial content, and the first change of the data from the initial content to the first updated content so that the first change of the data indicates, separately from the first updated content and the initial content, each point of difference between the initial content and the first updated content, wherein overwriting the storage space saves computing and storage resources by decreasing an amount of storage needed for tracking the first change of the data from the initial content to the first updated content using the mutation object, wherein the updated mutation object includes:

a first instance indicating a description of the initial content; and a second instance indicating a description of the first updated content and a description of the first change of the data from the initial content to the first updated content, wherein the first instance is associated with a full status indicator indicating that the first instance includes description without including description change, and wherein the second instance is associated with a combined status indicator indicating that the second instance includes both description and description change;

accessing, from the database, a first updated audit record based on the first updated content of the data;

storing, in the hardware storage device, the updated mutation object including a single dataset corresponding to the initial content and a single dataset corresponding to the first change of the data without storing duplicate datasets of the initial content and the first change of the data, wherein storing the updated mutation object in the hardware storage device overwrites the mutation object with the updated mutation object in the hardware storage device so that first data corresponding to the mutation object is replaced with second data corresponding to the updated mutation object;

causing rendering on a display device of a user interface that provides one or more indicators of the first instance and one or more indicators of the second instance including:

a first time indicator corresponding to a time at which the first instance was created;

the full status indicator indicating that the first instance includes description without including description change;

a second time indicator to one or more times at which the second instance was created; and the combined status indicator indicating that the second instance includes both description and description change; and storing, in the hardware storage device, the initial audit record and the first updated audit record.

2. The computer-implemented method of claim 1, wherein the one or more properties comprise an action of the audit.

3. The computer-implemented method of claim 1, wherein the one or more properties comprise one or more references to the medical safety event.

4. The computer-implemented method of claim 1, wherein the mutation object comprises a set of instances including the first instance and the second instance, each instance of the set of instances including an event description, a mutation status indicator, and a mutation action indicator.

5. The computer-implemented method of claim 4, wherein updating the mutation object to describe the first updated content comprises:

setting the event description of the first instance to include the description of the initial content;

setting the mutation status indicator of the first instance to the full status indicator;

setting the mutation action indicator of the first instance to indicate that the first instance is associated with a creation of the mutation object;

setting the event description of the second instance to include the description of the first updated content and the description of the first change of the data;

setting the mutation status indicator of the second instance to the combined status indicator; and setting the mutation action indicator of the second instance to indicate that the second instance is associated with an update of the mutation object.

6. The computer-implemented method of claim 5, wherein the updated mutation object comprises a first updated mutation object, and wherein the method further comprises:

determining a second change of the data from the first updated content to a second updated content; and updating the first mutation object to a second updated mutation object describing the second updated content, the initial content, the first change of the data from the initial content to the first updated content, and the second change of the data from the first updated content to the second updated content; and storing, in the hardware storage device, the second updated mutation object including the single dataset corresponding to the initial content, the single dataset corresponding to the first change of the data, and a single dataset corresponding to the second change of the data without storing duplicate datasets of the initial content, the first change of the data, and the second change of the data.

7. The computer-implemented method of claim 6, wherein updating the mutation object to describe the second updated content comprises:

generating a third instance of the set of instances so that the event description of the third instance includes a description of the second updated content and a description of the second change of the data from the first updated content to the second updated content;

setting the mutation status indicator of the third instance to the combined status indicator indicating that the third instance includes both description and description change;

setting the mutation action indicator of the third instance to indicate that the third instance is associated with an update of the mutation object;

truncating the second instance to include the description of the first change of the data from the initial content to the first updated content without including the description of the first updated content; and changing the mutation status indicator of the second instance to a difference status indicator indicating that the second instance includes description change without including description.

8. The computer-implemented method of claim 1, wherein the initial audit record and the first updated audit record are stored in a format of an expression language.

9. The computer-implemented method of claim 6, further comprising:

obtaining a second updated audit record based on the second updated content of the data; and storing, in the hardware storage device, the second updated audit record.

10. A non-transitory computer-readable medium storing program instructions that cause a data processing system to perform operations comprising:

receiving a request to perform an audit on data describing a medical safety event of a plurality of medical safety events within a healthcare institution;

obtaining, from a hardware storage device storing a plurality of audit records based on the request, an initial audit record corresponding to the medical safety event of the plurality of medical safety events;

parsing, by a parser, fields of the initial audit record to identify a structure of the initial audit record;

accessing, from a database from the structure of the parsed fields, one or more fields that describe one or more properties of the medical safety event;

instantiating a mutation object based on the one or more fields of the initial audit record, with the mutation object describing an initial content of the data;

accessing, by the mutation object according to logic for identifying differences between data files, a first change of the data from the initial content to a first updated content, wherein the first change of the data represents each point of difference between the initial content and the first updated content;

overwriting, in memory, storage space for the mutation object with an updated mutation object that describes the first updated content, the initial content, and the first change of the data from the initial content to the first updated content so that the first change of the data indicates, separately from the first updated content and the initial content, each point of difference between the initial content and the first updated content, wherein overwriting the storage space saves computing and storage resources by decreasing an amount of storage needed for tracking the first change of the data from the initial content to the first updated content using the mutation object, wherein the updated mutation object includes:

a first instance indicating a description of the initial content; and a second instance indicating a description of the first updated content and a description of the first change of the data from the initial content to the first updated content, wherein the first instance is associated with a full status indicator indicating that the first instance includes description without including description change, and wherein the second instance is associated with a combined status indicator indicating that the second instance includes both description and description change;

accessing, from the database, a first updated audit record based on the first updated content of the data;

storing, in the hardware storage device, the updated mutation object including a single dataset corresponding to the initial content and a single dataset corresponding to the first change of the data without storing duplicate datasets of the initial content and the first change of the data, wherein storing the updated mutation object in the hardware storage device overwrites the mutation object with the updated mutation object in the hardware storage device so that first data corresponding to the mutation object is replaced with second data corresponding to the updated mutation object;

causing rendering on a display device of a user interface that provides one or more indicators of the first instance and one or more indicators of the second instance including:

a first time indicator corresponding to a time at which the first instance was created;

the full status indicator indicating that the first instance includes description without including description change;

a second time indicator to one or more times at which the second instance was created; and the combined status indicator indicating that the second instance includes both description and description change; and storing, in the hardware storage device, the initial audit record and the first updated audit record.

11. The non-transitory computer-readable medium of claim 10, wherein the one or more properties comprise an action of the audit.

12. The non-transitory computer-readable medium of claim 10, wherein the one or more properties comprise one or more references to the medical safety event.

13. The non-transitory computer-readable medium of claim 10, wherein the mutation object comprises a set of instances including the first instance and the second instance, each instance of the set of instances including an event description, a mutation status indicator, and a mutation action indicator.

14. The non-transitory computer-readable medium of claim 13, wherein updating the mutation object to describe the first updated content comprises:

setting the event description of the first instance to include the description of the initial content;

setting the mutation status indicator of the first instance to the full status indicator;

setting the mutation action indicator of the first instance to indicate that the first instance is associated with a creation of the mutation object;

setting the event description of the second instance to the combined status indicator setting the mutation status indicator of the second instance to the combined status indicator; and setting the mutation action indicator of the second instance to indicate that the second instance is associated with an update of the mutation object.

15. The non-transitory computer-readable medium of claim 14, wherein the updated mutation object comprises a first updated mutation object, and the operations further comprising:

determining a second change of the data from the first updated content to a second updated content; and updating the first mutation object to a second updated mutation object describing the second updated content, the initial content, the first change of the data from the initial content to the first updated content, and the second change of the data from the first updated content to the second updated content; and storing, in the hardware storage device, the second updated mutation object including the single dataset corresponding to the initial content, the single dataset corresponding to the first change of the data, and a single dataset corresponding to the second change of the data without storing duplicate datasets of the initial content, the first change of the data, and the second change of the data.

16. The non-transitory computer-readable medium of claim 15, wherein updating the mutation object to describe the second updated content comprises:

generating a third instance of the set of instances so that the event description of the third instance includes a description of the second updated content and a description of the second change of the data from the first updated content to the second updated content;

setting the mutation status indicator of the third instance to the combined status indicator indicating that the third instance includes both description and description change;

setting the mutation action indicator of the third instance to indicate that the third instance is associated with an update of the mutation object;

truncating the second instance to include the description of the first change of the data from the initial content to the first updated content without including the description of the first updated content; and changing the mutation status indicator of the second instance to a difference status indicator indicating that the second instance includes description change without including description.

17. The non-transitory computer-readable medium of claim 10, wherein the initial audit record and the first updated audit record are stored in a format of an expression language.

18. The non-transitory computer-readable medium of claim 15, the operations further comprising:

obtaining a second updated audit record based on the second updated content of the data; and storing, in the hardware storage device, the second updated audit record.

19. A system comprising:

a hardware storage device; and one or more processors having access to the hardware storage device and configured to:

receive a request to perform an audit on data describing a medical safety event of a plurality of medical safety events within a healthcare institution;

obtain, from the hardware storage device storing a plurality of audit records based on the request, an initial audit record corresponding to the medical safety event of the plurality of medical safety events;

parse, using a parser, fields of the initial audit record to identify a structure of the initial audit record;

access, from a database from the structure of the parsed fields, one or more fields that describe one or more properties of the medical safety event;

instantiate a mutation object based on the one or more accessed fields of the initial audit record, with the mutation object describing an initial content of the data;

access, from a database by the mutation object according to executable logic for identifying differences between data files, a first change of the data from the initial content to a first updated content, wherein the first change of the data represents each point of difference between the initial content and the first updated content;

overwrite, in memory, storage space for the mutation object with an updated mutation object that describes the first updated content, the initial content, and the first change of the data from the initial content to the first updated content so that the first change of the data indicates, separately from the first updated content and the initial content, each point of difference between the initial content and the first updated content so that the first change of the data indicates, separately from the first updated content and the initial content, each point of difference between the initial content and the first updated content, wherein overwriting the storage space saves computing and storage resources by decreasing an amount of storage needed for tracking the first change of the data from the initial content to the first updated content using the mutation object, wherein the updated mutation object includes:

a first instance indicating a description of the initial content; and a second instance indicating a description of the first updated content and a description of the first change of the data from the initial content to the first updated content, wherein the first instance is associated with a full status indicator indicating that the first instance includes description without including description change, and wherein the second instance is associated with a combined status indicator indicating that the second instance includes both description and description change;

access, from the database, a first updated audit record based on the first updated content of the data;

store, in the hardware storage device, the updated mutation object including a single dataset corresponding to the initial content and a single dataset corresponding to the first change of the data without storing duplicate datasets of the initial content and the first change of the data, wherein storing the updated mutation object in the hardware storage device overwrites the mutation object with the updated mutation object in the hardware storage device so that first data corresponding to the mutation object is replaced with second data corresponding to the updated mutation object;

cause rendering on a display device of a user interface that provides one or more indicators of the first instance and one or more indicators of the second instance including:

a first time indicator corresponding to a time at which the first instance was created;

the full status indicator indicating that the first instance includes description without including description change;

a second time indicator to one or more times at which the second instance was created; and the combined status indicator indicating that the second instance includes both description and description change; and store, in the hardware storage device, the initial audit record and the first updated audit record.

* * * * *